(12) United States Patent
Hough et al.

(10) Patent No.: US 8,584,513 B2
(45) Date of Patent: Nov. 19, 2013

(54) SYSTEMS AND METHODS FOR EVALUATING ASPHALTENE DEPOSITION INHIBITORS

(75) Inventors: Lawrence A. Hough, Philadelphia, PA (US); Jean-Christophe Castaing, Burlington, NJ (US); Gary Woodward, Northwich Cheshire (GB); Ruela Talingting Pabalan, Burlington, NJ (US); Floryan De Campo, Shanghai (CN)

(73) Assignee: Rhodia Operations, Aubervilliers (FR)

( * ) Notice: Subject to any disclaimer, the term of this patent is extended or adjusted under 35 U.S.C. 154(b) by 281 days.

(21) Appl. No.: 12/932,386

(22) Filed: Feb. 24, 2011

(65) Prior Publication Data

US 2011/0203353 A1    Aug. 25, 2011

Related U.S. Application Data

(60) Provisional application No. 61/338,828, filed on Feb. 24, 2010.

(51) Int. Cl.
    *G01N 33/26* (2006.01)
(52) U.S. Cl.
    USPC ....... 73/61.62; 73/53.01; 73/61.41; 73/61.43; 73/61.44; 73/61.59; 73/64.41; 73/863; 73/863.71
(58) Field of Classification Search
    USPC ....................................................... 73/61.62
    See application file for complete search history.

(56) References Cited

U.S. PATENT DOCUMENTS

| | | | |
|---|---|---|---|
| 6,270,653 B1 * | 8/2001 | Gochin et al. | 208/44 |
| 6,313,367 B1 | 11/2001 | Breen | 585/950 |
| 6,839,137 B2 | 1/2005 | Mason et al. | 356/338 |
| 6,925,392 B2 | 8/2005 | McNeil, III et al. | 702/22 |
| 2003/0079879 A1 | 5/2003 | Grainger et al. | 166/304 |
| 2004/0255649 A1 | 12/2004 | Zougari et al. | 73/61.62 |
| 2008/0134770 A1 | 6/2008 | Horsup | 73/86 |

FOREIGN PATENT DOCUMENTS

| | | | | |
|---|---|---|---|---|
| WO | WO 01/27438 A1 | 4/2001 | | E21B 37/06 |
| WO | WO 2009/001096 | * 12/2008 | | G01N 1/40 |

OTHER PUBLICATIONS

Brookhaven Instrument Specification Sheet, http://web.archive.org/web/20090211001130/http://brookhaveninstruments.com/90Plus.html, Accessed Feb. 11, 2009.*

* cited by examiner

*Primary Examiner* — Hezron E Williams
*Assistant Examiner* — Alexander Mercado

(57) ABSTRACT

Disclosed are methods of determining the effectiveness of an asphaltene deposition inhibitor in oilfield applications. Such methods typically comprising the steps of introducing an oil well fluid into a microfluidic/millifluidic system; introducing a mixture of an asphaltene deposition inhibitor and carrier into the microfluidic/millifluidic system; introducing a precipitating agent, typically comprising heptane, into the microfluidic/millifluidic system; and optionally introducing toluene into the microfluidic/millifluidic system; then observing the presence or absence of asphaltene aggregation within the microfluidic/millifluidic system.

14 Claims, 1 Drawing Sheet

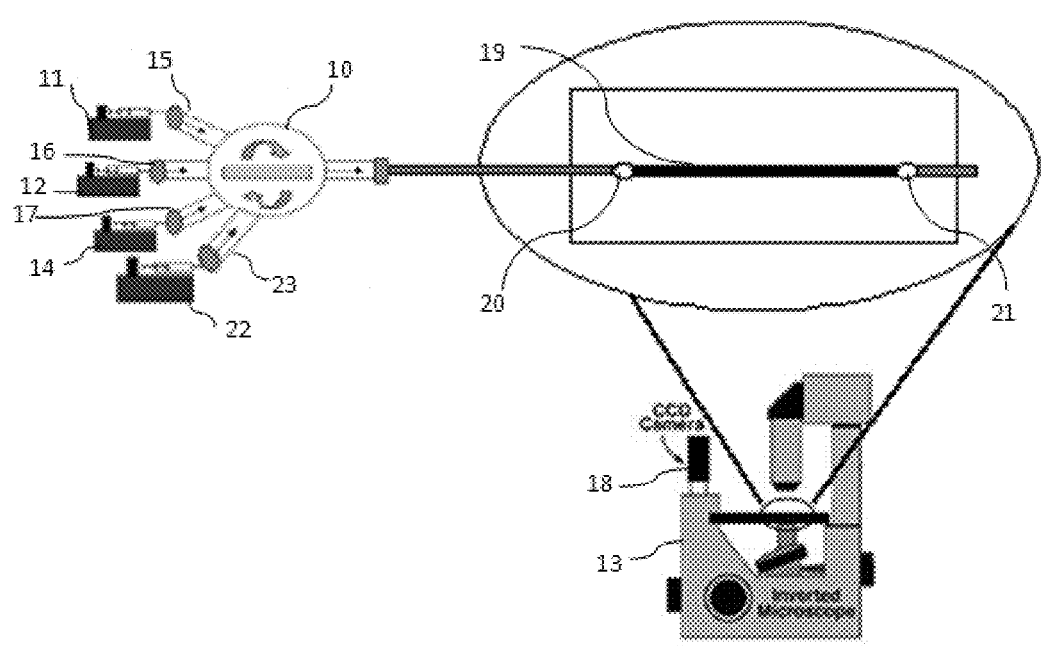

SYSTEMS AND METHODS FOR EVALUATING ASPHALTENE DEPOSITION INHIBITORS

CROSS-REFERENCE TO RELATED APPLICATIONS

This application claims the benefit of U.S. Provisional App. Ser. No. 61/338,828, filed Feb. 24, 2010.

FIELD OF THE INVENTION

The present invention relates to systems and methods for evaluating potential asphaltene deposition inhibitors and more particularly an improved on-site or close-to-site process for testing potential inhibitors of asphaltene deposition in crude oil and the like.

BACKGROUND OF THE INVENTION

Crude oil typically contains one or more solids such as asphaltenes, waxes including parrafins, hydrates and scale, among others. Further, in oil production, generally at some point oil such as crude oil is transported in liquid form through long stretches of pipes. The deposition of these solids from the crude oil onto the interior surfaces of the pipes can have a drastic and negative impact on the oil flow through these pipes.

Asphaltenes, in particular, make up one of the most polar fractions of crude oil, and often will precipitate upon an external stress such as temperature, pressure and/or compositional changes in the oil (resulting from blending or physical/chemical processing). Asphaltenes often precipitate, along with other solids such as paraffin waxes, when crude oil is transported via pipe, such as from a geologic structure to a wellhead via a production pipeline or from a wellhead or a storage vessel to a refinery via a pipeline. Asphaltene deposits can plug downhole tubulars, well-bores, choke off pipes and interfere with the functioning of separator equipment. Precipitated asphaltenes are not desirable, as they can foul and lead to fouling of process equipment.

Under many conditions, the solids present in a fluid will remain dissolved in the fluid. However, when deposition in a pipe occurs, it is generally undesirable because deposited solids can at least partially block the pipe and lead to reduction in the flow rate of the fluid in the pipe and require expensive and time-consuming cleaning of the pipe to restore the maximum or minimum acceptable flow rate of the fluid.

Asphaltenes are generally polyaromatic compounds and variably substituted with alkyl groups, along with heteroatoms such as oxygen, nitrogen, and sulfur and metal atoms (such as Ni, V, or Fe).

Asphaltenes are usually found in heavy crude oils and refinery normally in high quantities, and remain suspended in solution due to their small size and the possible solvating effects of other types of molecules in the petroleum oil or stream. These structures of several molecules are sometimes referred to as asphaltene particles. The asphaltene particles are generally smaller than twenty nanometers in size, but this can vary depending upon several factors such as their concentration in the oil.

It is known that insoluble asphaltenes may precipitate when two or more unprocessed petroleum crude oils and/or refinery process streams are blended together, such that the insoluble asphaltenes form asphaltene aggregates, or large precipitated clusters of asphaltene particles and molecules that stick together due to an attractive interaction. It is believed that this is reinforced when the nonpolar petroleum oil and/or refinery process stream is blended into the oil containing the asphaltenes. These aggregates can sometimes be observed with the unaided naked eye, and are typically physically and optically more dense than the surrounding oil mixture from which they precipitated. These aggregates tend to slowly sediment.

SUMMARY OF THE INVENTION

The present invention will be described in greater detail, which in one aspect is a method of determining the effectiveness of a potential asphaltene deposition inhibitor in oilfield applications comprising the steps of a) obtaining a sample of crude oil and introducing the sample into a microfluidic/millifluidic system; b) introducing a first fluid comprising a mixture of a potential asphaltene deposition inhibitor and carrier fluid into the microfluidic/millifluidic system; c) introducing a second fluid comprising a precipitating agent into the microfluidic/millifluidic system; and d) introducing a third fluid comprising an aromatic solvent into the microfluidic/millifluidic system; wherein by contacting the first fluid, second fluid and third fluid with the sample permits the observation of asphaltene aggregation.

In one embodiment, the microfluidic/millifluidic system comprises a microfluidic/millifluidic device operably connected to the viewing device and mixing well where the first, second and third fluid are combined. The microfluidic/millifluidic system can be operably connected to a processing unit. The processing unit, such as a computer, can be operated by a user to regulate the flow of the first, second and/or third fluid into mixing well. The processing unit can be operated by a user to regulate the flow of the first, second and/or third fluid into microfluidic/millifluidic device. The viewing device can be any suitable device to view the combination of one or more fluids and sample of crude oil, and which is operably connected to the processing unit. Typically, the viewing device is a microscope that can magnify and can illuminate the combination. The processing unit is capable of capturing an image of the combination (fluid(s) and crude oil sample).

The processing unit can be operated to regulate the flow of individual fluids into the mixing well. For example, this can be accomplished through regulating the pressure exerted on a syringe housing each fluid.

In one embodiment, the first fluid is contacted with the sample prior to the second fluid contacting the sample. In another embodiment, the first and third fluids are contacted with the sample prior to the second fluid contacting the sample. In yet another embodiment, the second and/or third fluids are contacted with the sample prior to the first fluid contacting the sample. In yet another embodiment, the second and/or third fluids are contacted with the sample prior to the first fluid contacting the sample. It is understood that any of the first, second or third fluid can be contacted with the sample in any order or simultaneously, as desired. Or, alternatively, any of the first, second and/or third fluids can be contacted with each other prior to contacting with the sample.

The process of the present invention allows for the determination, in a short period of time, whether a possible asphaltene inhibitor is feasible. Further, the process of the present invention only requires small amounts (e.g. milliliters or microliters) of a crude oil sample and the aforementioned fluids to perform an evaluation of a potential asphaltene inhibitor. Thus, contrary to the prior art method of determining asphaltene inhibition, the current invention allows for minimal turn-around time, nominal sample size, and use of low amounts and concentrations of crude oil samples. The present invention also allows on-site or close-to-site evaluation and optimization of treatment fluids, formation fluids, and other fluids utilized in the oil production process. The present invention can be incorporated as an on-site benchtop tool or close-to-site tool.

BRIEF DESCRIPTION OF THE DRAWINGS

FIG. 1 is an exemplary schematic diagram of one embodiment used to screen potential asphaltene inhibitors, wherein solvents, inhibitors, crude oil are programmed to be injected into smaller reactors and aggregation is monitored and recorded through a microscope.

DETAILED DESCRIPTION OF THE PREFERRED EMBODIMENTS

Crude oil from geological formations commonly contains solids, typically as one or more of waxes, asphaltenes, sulfur, minerals (e.g., scale), and hydrates. When crude oil is transported via pipeline, e.g., from a geological formation to a wellhead or from a wellhead or a storage vessel to a refinery via pipeline, changes in the pressure, temperature, composition, etc. (or other parameters of the flowing crude oil) can lead to deposition of solids on the pipe walls and surfaces.

Precipitation means the formation of a solid phase out of a liquid phase and, as used herein, refers to the agglomeration of solids while remaining suspended in the bulk fluid fraction. Deposition means the formation and growth of a layer of the precipitated solid on a surface and, as used herein, refers to the falling out of suspension of the agglomerated solids and the resulting coating of the agglomerated materials on the interior wall of the pipe or tubing. Aggregation, as used herein, can refer to precipitation or deposition, or, alternatively, to a combination of precipitation and deposition.

Deposited solids including asphaltene can lead to reductions in the flow rate of the crude oil or other fluid in the pipe and can require time-consuming cleaning, as well as shutdown of the pipe to restore the maximum flow rate, which can be very expensive. Knowledge of parameters in which precipitation or deposition are likely to occur in a sample of a particular crude oil, as well as use of deposition inhibitors such as aspheltene deposition inhibitors, can minimize reduction in the flow rate of the crude oil.

The effectiveness of inhibitors to asphaltene deposition has traditionally included down-hole conditions or complicated devices, and screening through such processes is generally slow (typically taking a week or longer) and only allows for the screening of one or a few asphaltene inhibitors at a time. Many of the prior art techniques are for down-hole conditions. These conditions (high pressure and temperature) make high throughput screening nearly impossible. Further, since the composition of crude oil can vary greatly from underground formation to underground formation, or from oil well to oil well, it is difficult to predict that a certain asphaltene deposition inhibitor will be effective at any particular site. It is often a painstaking task of sampling crude oil from a particular site or well, and then testing that sample using conventional methods, which may take up to a week.

Thus, the present invention addresses the need for an improved method for the testing of crude oil from a particular site for compatibility with or effectiveness of one or more potential asphaltene inhibitors. The process of the present invention is more efficient than conventional testing methods, and requires only a minimal amount of a crude oil sample. The method and system of the present invention also allows for quick screening of several compounds, as opposed to the traditional slow screening typically used for one compound at a time. The amount of time needed to screen for potential asphaletene deposition inhibitors is thus minimized. The use of an optical microscope 13 or other similar device can be used to measure the effectiveness of the potential inhibitor 11 in preventing the aggregation of asphaltenes in crude oil 14, or on surfaces.

The present invention simplifies the screening process so that an on-site or close-to-site procedure can be utilized.

In one embodiment, a high throughput millifluidic or microfluidic device 10 (hereinafter "microfluidic/millifluidic device") is used. The high throughput microfluidic/millifluidic device 10 can be incorporated into a microfluidic/millifluidic system 1. In its simplest embodiment, the microfluidic/millifluidic system 1 comprises several components including (1) a viewing device 13, (2) one or more mixing wells 19 having an inlet 20 and outlet 21, (3) one or more fluid sources 11, 12, 14 and (4) a microfluidic/millifluidic device 10. Each component can be operably connected to one or more of the other components. For example, the microfluidic/millifluidic device 10 may be removably detached from the viewing device, typically a microscope, more typically an optical microscope 13. In one embodiment, the viewing device is an optical microscope connected to a camera 18 capable of capturing images obtained through the microscope 10. As another example, the fluid sources 11, 12, 14 can be operably connected to the mixing well via one or more tubes 15, 16, 17, such that fluid can flow from the fluid source to the mixing well 10. A fourth fluid source 22 connected by tube 23 to microfluidic/millifluidic device 10 is optional.

The fluid source(s) can comprise any of a number of fluids utilized to test for the agglomeration of asphaltene. In some embodiments, one or more fluid sources comprise (i) a carrier fluid, typically toluene, containing a potential asphaltene deposition inhibitor, (ii) a precipitating agent, (iii) an aromatic solvent, (iv) a crude oil sample or diluted crude oil sample. In other embodiments, less than the above-described fluid sources are utilized. In other embodiments, more than the above-described fluid sources are utilized.

In one particular embodiment, there are four fluid sources. The first fluid source contains a mixture of a potential asphaltene deposition inhibitor and carrier fluid, which is typically toluene. The second fluid source contains a precipitating agent which is typically heptane or an isomer of heptane, e.g., isoheptane. The third fluid source is an aromatic solvent such as toluene, benzene and the like. The fourth fluid source contains a crude oil sample or a diluted crude oil sample. Typically, a fluid source (e.g., first fluid source, second fluid source, etc.) comprises a syringe housing a particular fluid. The syringe is operably connected at one end to a regulator capable of exerting pressure on the plunger, and at the other end is operably connected to tubing that directs the flow of the fluid from the syringe housing and through the tubing upon exertion of pressure on the syringe plunger by the regulator.

In one embodiment, one or more, or all of these components can be operably connected to one or more central processing units. A central processing unit (CPU) can regulate and operate various parameters such as flow rates, mixing rate, start/stop, image capture, and the like. Typically, the central processing unit is a computer. The computer can contain software that is capable of operating the pumps, mixer, any movable/variable component of the microfluidic/millifluidic system, etc., as well as storing and tracking images captured by the viewing device. In one embodiment, one central processing unit regulates and operates the flow rates of one or more liquids from their respective liquid source to the mixing well, regulates and operates the flow rates of the mixed liquids passing through the microfluidic/millifluidic device, stores images of the mixture and interaction between the crude oil sample and potential asphaltene deposition inhibitor through the microscope so that one can track and observe any agglomeration, and regulates mixing of one or more fluids and the crude oil sample in the mixing well. It is also understood that more than one CPU can be used; for example, one CPU can be used to regulate the flow and mixing rates of the microfluidic/millifluidic system, the other CPU to capture and store images of any potential agglomeration in the microfluidic/millifluidic device. It is also understood that one or more CPUs may be remotely connected to the microfluidic/millifluidic system, e.g., through the Internet or other means.

Microfluidic/millifluidic devices are typically comprised of fluidic channels with lateral dimensions ranging from as small as tens to hundreds to thousands of micrometers and are designed to operate with extremely small volumetric flow rates. Microfluidic devices of the present invention, in general, are devices which allow for analysis of fluids in micro-sized channels etched on a planar substrate where a pressure or force directs these fluids through the various interconnected channels or chambers. Similarly, millifluidic devices of the present invention, in general, are devices which allow for analysis of fluids in milli-sized channels etched on a planar substrate where a pressure or force directs these fluids through the various interconnected channels or chambers. In one embodiment, microfluidic/millifluidic devices are composed of glass- or polymer plate(s) that have a pre-defined pattern of two dimensional or three dimensional etched, molded or printed channels and wells in them. Such channels include at least one cross sectional dimension that is in the range of from about 0.1 µm to about 5000 µm. In one embodiment, dimensions may range from about 500 µm to about 5000 µm. Dimensions may, in another embodiment, range from about 1 µm to about 100 µm. Dimensions may also range from about 5 µm to about 100 µm. Use of dimensions of this order allows the incorporation of a greater number of channels, chambers or sample wells in a small area, and utilizes smaller volumes of reagents, samples, and other fluids for performing the preparative or analytical manipulation of the sample that is desired.

In one exemplary embodiment, the microfluidic/millifluidic device comprises two base layers, and in between is a middle layer attached to either or both of the base layers. The middle layer defines a pattern or geometric structure that has one or several cavities or channels. In some embodiments, the middle layer forms the side walls and/or one of the top and bottom walls of each cavity or channel (where one of the base layers forms the other of the top/bottom walls). In other embodiments, the middle layer forms the side walls, one base layer forms the top wall and the other base layer forms the bottom wall. In either embodiment, the middle layer is sufficiently elastic to provide for adequate sealing to either or both of the base layer(s). In other embodiments, there is more than one middle layer, wherein two middle layers are separated by intermediate base layers. Channels can be formed as explained previously or in adjacent spacing layers through communicating by apertures or bores in the intermediate base layers.

The channels or wells may be pre-treated to alter surface properties of the glass- or polymer channels, and they may contain typical micro-electric devices such as pumps, valves or heating elements. The transport of the fluid inside the channels may be accomplished by using electro-kinetic forces (i.e. applying an electric field) or by applying a pressure gradient across the channels.

The types of measurements in such microfluidic/millifluidic devices may include the determination of sample concentrations, reactivity, relative flow, viscosity, hydraulic, or electric resistivity.

In one embodiment, the microfluidic/millifluidic system may have one or more wells or mixing wells that are etched, attached or cut into the plate with channels connecting the wells. These wells serve as reservoirs to hold a respective fluid or mixture of fluids, as well as crude oil sample fluid, standard fluid, buffer for dilution, dye, or reagents and a waste well. The wells are connected with the aforementioned channels such that mixing among these fluids can take place. The fluids are moved through the channels by pumps or by electrokinetic forces. A photomultiplier may be directed to any point in the network of channels, but preferably to a section of the channel where all the mixing has taken place and the reaction can be observed and/or captured as an image.

The microfluidic/millifluidic devices used herein are characterized by the use of fluid transport and direction systems that either employ mechanical pumps or valves, or the application of external pressure, or electro-kinetic flow to selectively move and direct the fluids through an interconnected series of channels contained in the device or system (as explained above).

In use, the measurement protocol can be pre-determined and written into a simple software routine that controls the pumps, mixer, fluid flow rates through use of a CPU. The test fluid, standard fluid, and other reagents or fluids, if desired, can be introduced into the receptacles or wells on the microfluidic/millifluidic plates. The introduction of small volumes of test compounds can be accomplished manually, using a standard pipette, or automatically. In some embodiments, the receptacles, chambers and/or wells typically need less than 100 microliters, typically less than 50 microliters, and more typically less than 25 microliters of fluid.

The microfluidic/millifluidic device of the present invention may be incorporated in a bench-top instrument, which allows for one or multiple microfluidic/millifluidic applications. The bench-top instrument may include a microfluidic/millifluidic system, a microfluidic/millifluidic device with wells and channels, an excitation source, suitable filters and photomultipliers and a storage unit for the test results. An analysis or viewing device may be mounted close or proximate to the substrate-viewing region to, for example, detect formation of aggregates along a portion of the substrate. A computer may be operably linked to one or more components of the bench-top instrument, for example, to monitor and capture formation of aggregates and the like.

In the method of the present invention the steps described can be utilized to obtain a number of key measurements, which in a typical embodiment is the effectiveness of a potential asphaltene deposition inhibitor in asphaltene aggregation. In another embodiment, the present invention can be used with respect to other components of crude oil that likewise have a tendency to deposit such as paraffins and the like; which in such case would be to test the effectiveness of paraffin deposition inhibitor or mixture thereof.

In one embodiment, the present invention is a method of determining the effectiveness of a potential asphaltene deposition inhibitor in oilfield applications comprising the steps of introducing an oil well fluid into a microfluidic/millifluidic system; introducing a first fluid comprising a mixture of a potential asphaltene deposition inhibitor and carrier fluid into the microfluidic/millifluidic system; introducing a second fluid comprising a precipitating agent into the microfluidic/millifluidic system; then observing the presence or absence of asphaltene aggregation within the microfluidic/millifluidic system. In another embodiment, a third fluid comprising an aromatic solvent is introduced into the microfluidic/millifluidic system.

Typically, the precipitating agent is an n-alkane but can be any suitable agent that promotes the agglomeration of asphaltene from crude oil. In one embodiment, the precipitating agent is heptane or n-heptane. In another embodiment, the precipitating agent is an isomer or enantiomer of heptane including but not limited to isoheptane, neoheptane, 3-Methylhexane, 2,3-Dimethylpentane, 2,4-Dimethylpentane, 3,3-Dimethylpentane, 3-Ethylpentane and/or 2,2,3-Trimethylbutane.

Typically, the carrier fluid is toluene but can be any suitable carrier fluid for example an aryl hydrocarbon, including but not limited to benzene, xylene, aniline, phenol, alkylbenzenes and/or the like.

The aromatic solvent is typically toluene but can be any other suitable aromatic solvent suitable for crude oil including but not limited to benzene, xylene, naphthalene, aniline, alkylbenzene, benzene derivatives, polyaromatic hydrocarbons such as benzocyclopropene, benzocyclopropane, benzocyclobutadiene and benzocyclobutene, and/or the like.

In another more specific embodiment, the present invention is a method of determining the effectiveness of a potential asphaltene deposition inhibitor in oilfield applications comprising the steps of a) obtaining a sample of crude oil and introducing the sample into a microfluidic/millifluidic system; b) introducing a first fluid comprising a mixture of a potential asphaltene deposition inhibitor and toluene into the microfluidic/millifluidic system; c) introducing a second fluid comprising heptane into the microfluidic/millifluidic system; and d) introducing a third fluid comprising toluene into the microfluidic/millifluidic system; wherein by contacting the first fluid, second fluid and third fluid with the sample permits the observation of asphaltene aggregation.

Typically, the fluids are introduced from a fluid source, which in some embodiments is a syringe housing a particular fluid that is connected to the microfluidic/millifluidic device as explained herein. For example, a first syringe is filled with crude oil, a second syringe is filled with the potential inhibitor and toluene, a third syringe is filled with heptane, and a fourth syringe is filled with pure toluene. It is know the asphaltenes precipitate or agglomerate from crude oil in the presence of approximately 65% heptane. The described fluids are mixed such that a potential inhibitor can be tested for asphaltene aggregation by direct imaging of the aggregates either in the bulk or near a surface.

It is understood that the potential asphaltene deposition inhibitor of the present invention can be a chemical or chemical compound, or a simple species or compound of a known or potential asphaltene deposition inhibitor. However, it is also understood that the asphaltene deposition inhibitor of the present invention can mean a cocktail or mixture of different or several species or compounds of asphaltene deposition inhibitors.

In one embodiment, the microfluidic/millifluidic system comprises microfluidic/millifluidic device operably connected to the viewing device and mixing well where the first, second and third fluid are combined. The microfluidic/millifluidic system can be operably connected to a processing unit. The processing unit, such as a computer, can be operated by a user to regulate the flow of the first, second and/or third fluid into mixing well. The processing unit can be operated by a user to regulate the flow of the first, second and/or third fluid into microfluidic/millifluidic device. The viewing device can be any suitable device to view the combination of one or more fluids and sample of crude oil, and which is operably connected to the processing unit. Typically, the viewing device is a microscope can magnify and can illuminate the combination. The processing unit is capable of capturing an image of the combination (fluid(s) and crude oil sample).

The processing unit can be operated to regulate the flow of individual fluids into the mixing well. This can be accomplished through regulating the pressure exerted on a syringe housing each fluid.

In one embodiment, the first fluid is contacted with the sample prior to the second fluid contacting the sample. In another embodiment, the first and third fluids are contacted with the sample prior to the second fluid contacting the sample. In yet another embodiment, the second and/or third fluids are contacted with the sample prior to the first fluid contacting the sample. In yet another embodiment, the second and/or third fluids are contacted with the sample prior to the first fluid contacting the sample. It is understood that any of the first, second or third fluid can be contacted with the sample in any order or simultaneously, as desired.

The potential asphaltene deposition inhibitor of the present invention prevents asphaltene aggregation. Some examples of known asphaltene inhibitors include but are not limited to aliphatic sulphonic acids; alkyl aryl sulphonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; and polyalkoxylated asphaltenes. In some embodiments, the potential asphaltene deposition inhibitor used in the process of the present invention comprises a mixture of two or more of the above referenced compounds, or a mixture of one or more of the above compounds with a potential or yet identified asphaltene deposition inhibitor. In some embodiments, the potential asphaltene deposition inhibitor is a yet to be determined inhibitor.

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

What is claimed is:

1. A method of comparing the asphaltene aggregation inhibited by a plurality of potential asphaltene deposition inhibitors in oilfield applications comprising the steps of:
   introducing an oil well fluid into a microfluidic/millifluidic system comprising a mixing well, a processing unit comprising a means for regulating the flow of fluids into the mixing well, and a viewing device;

introducing a first fluid comprising a mixture of a first potential asphaltene deposition inhibitor and a carrier fluid into the microfluidic/millifluidic system such that the first fluid contacts the oil well fluid in the mixing well;

introducing a second fluid comprising a precipitating agent into the microfluidic/millifluidic system such that the second fluid contacts the oil well fluid in the mixing well; and capturing images with the viewing device of asphaltene aggregation within a channel of the microfluidic/millifluidic system; and then introducing the oil well fluid, first fluid comprising a mixture of a second potential asphaltene deposition inhibitor and a carrier fluid, and the second fluid comprising the precipitating agent into the mixing well of the microfluidic/millifluidic system, and capturing images with the viewing device of asphaltene aggregation within the system; and comparing the asphaltene aggregation inhibited by the first and second asphaltene deposition inhibitors.

2. The method of claim 1 wherein the precipitating agent is heptane and the carrier fluid is toluene.

3. The method of claim 1 wherein the oil well fluid comprises crude oil.

4. The method of claim 1 wherein volumetric amounts used of the oil well fluid, the first fluid, the second fluid and the third fluid each comprise less than 500 microliters.

5. The method of claim 1 wherein the volumetric amounts used of the oil well fluid, the first fluid, the second fluid and the third fluid each comprise less than 50 microliters.

6. The method of claim 1 further comprising
introducing a third fluid comprising an aromatic solvent into the microfluidic/millifluidic system.

7. The method of claim 6 wherein the aromatic solvent is selected from the group consisting of toluene, benzene, xylene, naphthalene, aniline, alkylbenzene, an benzene derivative, a polyaromatic hydrocarbon, benzocyclopropene, benzocyclopropane, benzocyclobutadiene and benzocyclobutene.

8. The method of claim 1 wherein the first fluid is contacted with the sample prior to the second fluid contacting the sample.

9. The method of claim 1 wherein the first fluid is contacted with the sample prior to the third fluid contacting the sample.

10. The method of claim 1 wherein the third fluid is contacted with the sample prior to the second fluid contacting the sample.

11. The method of claim 1 wherein the first fluid, second fluid and third fluid are simultaneously contacted with the sample.

12. The method of claim 1 wherein volumetric amounts used of the crude oil sample, the first fluid, the second fluid and the third fluid each comprise less than 500 microliters.

13. The method of claim 1 wherein the volumetric amounts used of the crude oil sample, the first fluid, the second fluid and the third fluid each comprise less than 50 microliters.

14. The method of claim 1 further comprising comparing the asphaltene aggregation inhibited by one or more additional potential asphaltene deposition inhibitors by repeating the introducing and observing steps for the one or more additional potential asphaltene deposition inhibitors.

* * * * *